US007445441B2

(12) United States Patent
West et al.

(10) Patent No.: US 7,445,441 B2
(45) Date of Patent: Nov. 4, 2008

(54) THREE-DIMENSIONAL PRINTING APPARATUS AND METHODS OF MANUFACTURE INCLUDING STERILIZATION OR DISINFECTION, FOR EXAMPLE, USING ULTRAVIOLET LIGHT

(75) Inventors: Thomas George West, Lawrenceville, NJ (US); Qing Liu, Hillsborough, NJ (US); Peter A. Materna, Metuchen, NJ (US); Alfred Anthony Litwak, Manasquan, NJ (US); Christopher M. Gaylo, Princeton Junction, NJ (US)

(73) Assignee: Therics, LLC, Akron, OH (US)

( * ) Notice: Subject to any disclaimer, the term of this patent is extended or adjusted under 35 U.S.C. 154(b) by 556 days.

(21) Appl. No.: 10/891,440

(22) Filed: Jul. 14, 2004

(65) Prior Publication Data

US 2005/0061241 A1    Mar. 24, 2005

Related U.S. Application Data

(60) Provisional application No. 60/487,447, filed on Jul. 14, 2003.

(51) Int. Cl.
*B29C 35/02* (2006.01)
*B29C 67/00* (2006.01)
*B28B 17/02* (2006.01)
(52) U.S. Cl. .................................. 425/174.4; 425/375
(58) Field of Classification Search ........................ None
See application file for complete search history.

(56) References Cited

U.S. PATENT DOCUMENTS

| | | | | |
|---|---|---|---|---|
| 5,204,055 A | * | 4/1993 | Sachs et al. | 419/2 |
| 5,387,380 A | * | 2/1995 | Cima et al. | 264/69 |
| 6,658,314 B1 | * | 12/2003 | Gothait | 700/119 |
| 6,905,645 B2 | * | 6/2005 | Iskra | 264/128 |
| 7,270,528 B2 | * | 9/2007 | Sherwood | 425/174.4 |
| 2001/0050031 A1 | * | 12/2001 | Bredt et al. | 106/162.9 |
| 2002/0105114 A1 | | 8/2002 | Kubo et al. | |

(Continued)

FOREIGN PATENT DOCUMENTS

DE            3933142            4/1990

(Continued)

*Primary Examiner*—Mary Lynn F Theisen
(74) *Attorney, Agent, or Firm*—Robert H. Eichenberger; Eric L. Killmeier; Middleton Reutlinger (57) ABSTRACT

The invention includes a three-dimensional printing (3DP) machine that has at least one ultraviolet (UV) light source directed at powder or slurry being processed by the 3DP machine and/or directed at any of various surfaces or machine components, in a manner suitable to kill or damage microorganisms to a desired extent. The UV light sources may be either stationary or movable, and may be either pulsed or substantially continuous, and may operate in any desired sequence and timing with respect to other operations performed by the machine. The invention may include ultraviolet illumination in such a way as to interact with powder to sterilize or disinfect powder either while the powder is stationary or, alternatively, as powder is being moved from one place to another within the 3DP machine, or both. The invention also includes methods of performing three-dimensional printing using such illumination. The invention also includes the combination of other methods of sterilization or disinfection with the use of ultraviolet light. The invention also includes the use of ultraviolet light sources for a combination of polymerization/cross-linking in addition to sterilization/disinfection.

45 Claims, 6 Drawing Sheets

U.S. PATENT DOCUMENTS

2003/0151167 A1* 8/2003 Kritchman et al. .......... 264/401
2005/0003189 A1* 1/2005 Bredt et al. ................. 428/402
2005/0110200 A1* 5/2005 Fong ........................... 264/494
2006/0208388 A1* 9/2006 Bredt et al. ................. 264/123
2007/0173967 A1* 7/2007 Kritchman et al. .......... 700/119

FOREIGN PATENT DOCUMENTS

DE             20201493             5/2003

* cited by examiner

THREE-DIMENSIONAL PRINTING APPARATUS AND METHODS OF MANUFACTURE INCLUDING STERILIZATION OR DISINFECTION, FOR EXAMPLE, USING ULTRAVIOLET LIGHT

CROSS-REFERENCE TO RELATED APPLICATION

This application claims the benefit of U.S. Provisional Patent Application No. 60/487,447 filed Jul. 14, 2003, where this provisional application is incorporated herein by reference in its entirety.

BACKGROUND OF THE INVENTION

1. Field of the Invention

This invention pertains to the manufacture of sterile or disinfected articles by three-dimensional printing.

2. Description of the Related Art

Manufacturing of medical articles must be done in conditions that are, depending on the needs of a particular article, clean, aseptic, sterile, or what is described in regulations as being under conditions of Good Manufacturing Practice. Sterility represents the highest degree of killing of microorganisms, and disinfection represents a somewhat lesser degree. Commonly used methods for killing or damaging microorganisms have included gamma radiation, electron beam radiation and other forms of ionizing radiation, and have also included heat and harsh chemicals in gaseous or liquid or other form.

Another technique that has been used for killing or damaging microorganisms, although it has been considered less aggressive than the above techniques, has been exposure to ultraviolet light. Ultraviolet light is more energetic than visible light. Proteins and nucleic acid, which all microorganisms contain, absorb light and can thereby suffer damage that kills the microorganisms or prevents their reproduction. In some instances several of these techniques have been applied to manufactured articles at the last stage of a manufacturing operation (terminal sterilization). In some instances several of these techniques have, additionally or instead, been applied either to materials or to equipment either before manufacturing or during or between any of various stages of manufacturing.

Figure 1:
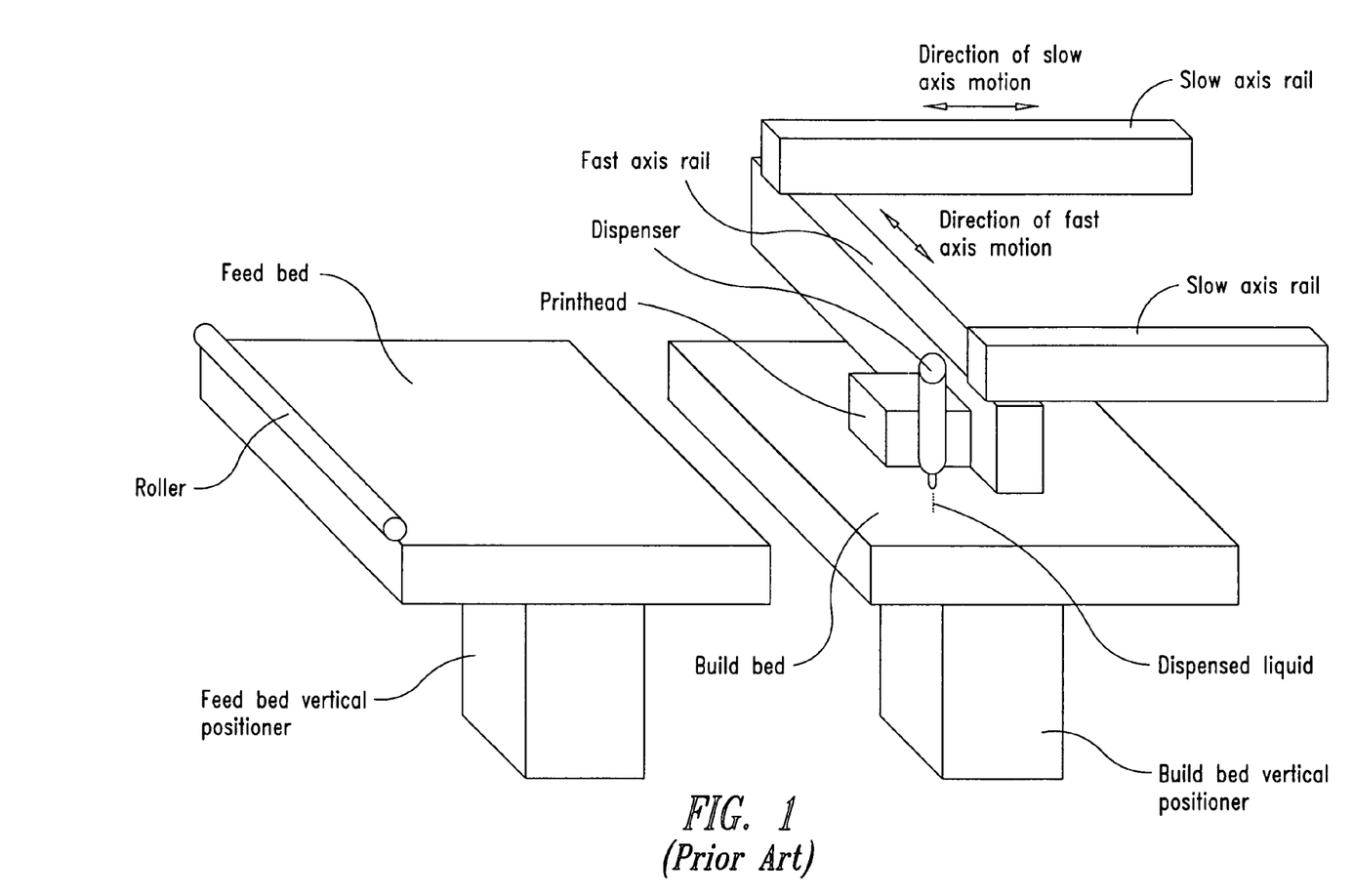
FIG. 1 illustrates a conventional three-dimensional printing machine of the prior art.

Three-dimensional printing (3DP) has had industrial and commercial applications including both rapid prototyping and fabrication of actual products. Three-dimensional printing described in U.S. Pat. No. 5,204,055 and elsewhere, is the manufacture of objects by assembling them from powder in a layer-by-layer fashion. It is illustrated in FIG. 1. In this process, layers of powder have been deposited by roller spreading or by other means. When the powder deposition has been by roller spreading, powder has been presented by raising a feed bed, and has been pushed by a roller from the feed bed to a build bed, where it has been spread in a thin layer. In selected places in the build bed, powder particles have then been joined to other powder particles and to other bound regions by the action of a binder liquid that has been dispensed from a dispenser such as a dispenser resembling an ink-jet printer. Binding has occurred as a result of a non-volatile substance being deposited by the binder fluid or dissolved by the binder fluid as the binder fluid lands on the powder bed, or has occurred as a result of dissolution of powder particles followed by re-solidification. Unbound powder has supported bound regions during printing and has later been removed after completion of 3DP.

In the medical field, 3DP is beginning to be used for direct manufacturing of some medical articles. Direct manufacturing of medical articles by 3DP can be more demanding than direct manufacturing of general industrial and commercial articles, at least because of the need for appropriate levels of cleanliness. Until now, traditional aseptic manufacturing techniques have not been adapted to three-dimensional printing, except to the extent described in the co-pending commonly assigned patent application referenced herein, which is incorporated by reference. More specifically, the use of ultraviolet light has not been applied to the process or apparatus of three-dimensional printing for purposes of sterilization or disinfection, although ultraviolet light has been employed for the purpose of chemically curing or cross-linking a binder substance such as in U.S. Pat. Nos. 6,467,897 and 6,696,073.

In addition to the general difficulty of implementing aseptic techniques on a piece of machinery having the complexity of a 3DP machine, there is also the issue that some articles manufactured for medical applications may contain fragile organic substances such as Active Pharmaceuticals Ingredients, growth factors, and even cells, any of which may be important in determining the performance of the medical article when it interacts with a living body. Such substances may be decomposed or damaged by many of the traditional sterilization techniques such as ionizing radiation, heat, and harsh chemicals. It is less likely, although still possible, that such substances may be decomposed or damaged by exposure to ultraviolet light. For example, it is known that microorganisms that contaminate blood are destroyed by ultraviolet light while the blood platelets, blood plasma and red blood cells are not damaged.

Accordingly, it would be desirable to provide ways of disinfecting or sterilizing machine apparatus used in three-dimensional printing. It would also be desirable to provide ways of sterilizing or disinfecting powder as the powder is in the three-dimensional printing machine. This might be desirable either when the powder is in a stationary situation or when the powder is in a situation where it is being moved. It would be desirable to achieve the desired degree of killing or damaging of microorganisms as much as possible relatively early in a manufacturing process, prior to the possible introduction of fragile substances into the article, and perhaps thereby avoid the need for terminal sterilization, which might damage the fragile substances. It would be desirable to accomplish the sterilization or disinfection using, at least partially, ultraviolet light. It would be desirable to have a sterilization or disinfection method which is well adapted to manufacturing an article in a layer-by-layer fashion so that the method can sterilize the material of each layer around the time of the manufacturing processes which affect that particular layer.

BRIEF SUMMARY OF THE INVENTION

The invention includes a three-dimensional printing (3DP) machine that comprises at least one ultraviolet light source directed at powder being processed by the 3DP machine and/or directed at any of various surfaces or machine components, in a manner suitable to kill or damage microorganisms to a desired extent. The UV light sources may be either stationary or movable, and may be either pulsed or substantially continuous, and may operate in any desired sequence and timing with respect to other operations performed by the machine. The invention may include ultraviolet illumination in such a way as to interact with powder to sterilize or disinfect powder either while the powder is stationary or, alternatively, as powder is being moved from one place to another within the 3DP machine, or both. The invention also includes methods of performing three-dimensional printing using such illumination. The invention also includes the combination of other methods of sterilization or disinfection with the use of ultraviolet light. The invention also includes the use of ultraviolet light sources for a combination of polymerization/cross-linking in addition to sterilization/disinfection.

BRIEF DESCRIPTION OF THE DRAWINGS

The invention is further described by the following illustrations, in which.

DETAILED DESCRIPTION OF THE INVENTION

Apparatus

Figure 2:
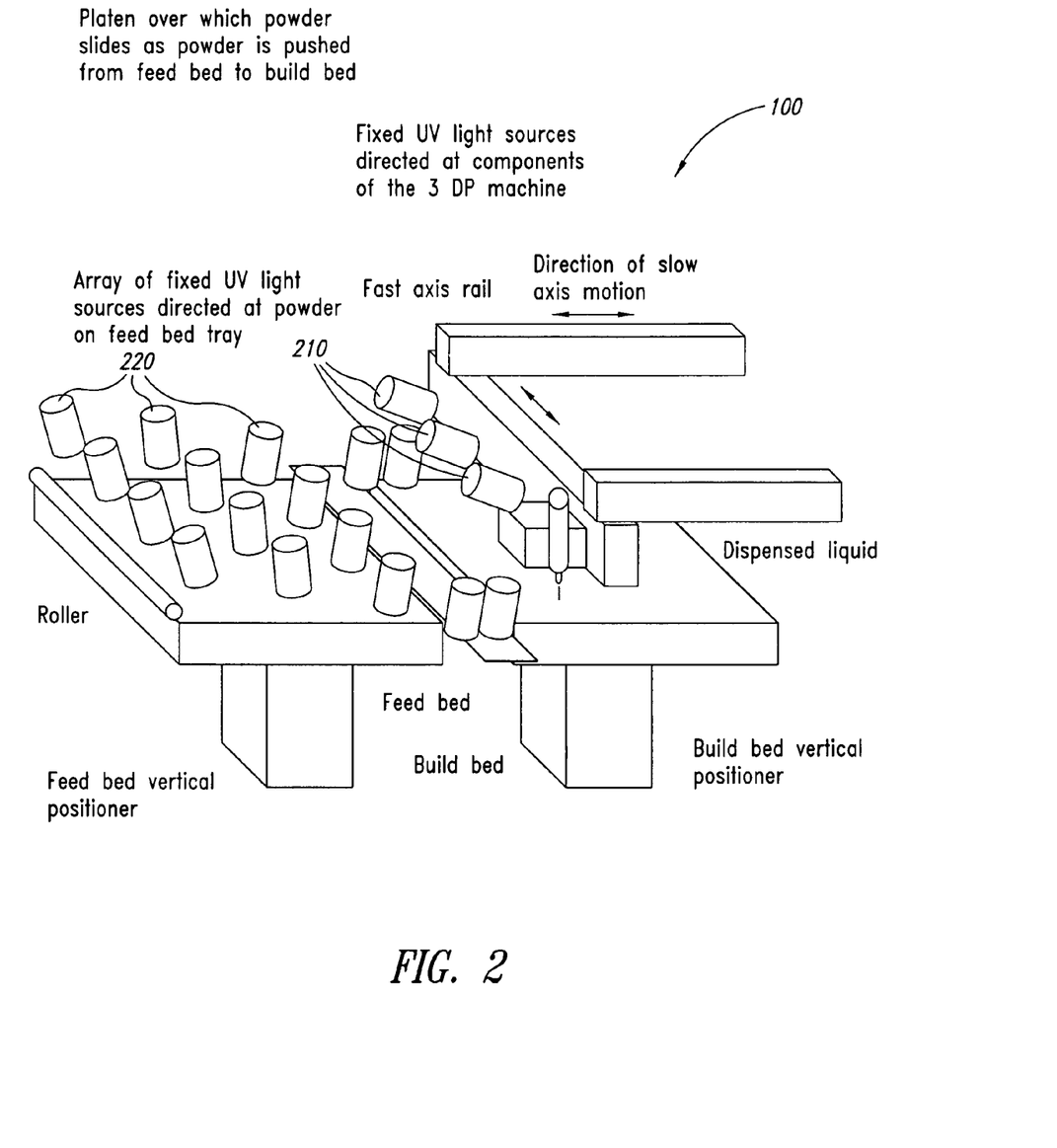
FIG. 2 illustrates a three-dimensional printing machine equipped with a plurality of stationary sources of ultraviolet light directed at powder and/or at components of the machine in accordance with principles of the present invention.

The invention includes a 3DP machine that comprises at least one ultraviolet light source. In general, UV light sources on a 3DP machine may be either stationary with respect to the overall machine or movable with respect to the overall machine. FIG. 2 illustrates a 3DP machine comprising a plurality of stationary sources of UV light. Fixed UV light source 210 is shown as being mounted with respect to the overall machine 100 and may be directed at powder which is being processed by the 3DP machine. In this illustration the illuminated powder is in the feed bed, but alternatively or in addition, powder in the build bed could be so illuminated. Other stationary UV light sources 220 may be directed at any surface or component in the machine at which may be desirable to kill or damage microorganisms. Such UV light sources are shown in FIG. 2 as being directed at the rails and related components near the printhead. Such UV light sources could be directed at components, which may come into contact with powder, such as the roller, the surfaces near the powder beds, etc.

Any of these stationary UV light sources 210, 220 either may be capable of operating substantially continuously during substantially the whole time while the 3DP machine 100 is operating, or may be capable of operating substantially continuously but only at designated times during the operation of the 3DP machine. It is also possible that the ultraviolet source may be capable of operating in a pulsed mode. The pulsed-powered ultraviolet source may be capable of operating pulsatingly either substantially the whole time while the 3DP machine is operating, or it may be capable of operating pulsatingly at designated times during operation of the 3DP machine. The 3DP machine may comprise means for such sequencing and control, such as instructions in the software which controls the overall operation of the 3DP machine, or other timing means such as are known in the relevant art.

At various times during the operation of a 3DP machine, powder is present in the form of a flat bed geometry. It is known that in application of ultraviolet light to beds of powders, ultraviolet light is able to kill or damage microorganisms at the immediate surface of the powder bed and also is able to kill or damage microorganisms into the powder bed to some depth. The operating parameters of the ultraviolet light source (such as wavelength, pulsation characteristics, delivered energy), and the depth of powder which is spread during any given spreading operation, and even the dimensions of the feed bed (e.g. the dimension of the feed bed in the direction of advancement of the roller) may be chosen suitably so that the powder which is spread during any powder spreading operation either has been suitably exposed to ultraviolet light before being spread or is suitably exposed to ultraviolet light after being spread. For example, the parameters may be chosen so as to kill or damage microorganisms of interest to a depth that is greater than the thickness of a layer of powder used in making an article by 3DP. Typically such layers may have a thickness of less than or approximately several hundred micrometers.

UV light sources that are directed at machine components rather than at powder may be capable of operating suitably so as to kill or damage desired microorganisms that may exist at the surface of the component at which these UV light sources are directed. This can include appropriate choice of wavelength, delivered energy, pulsed/continuous operation, etc.

Any of these ultraviolet sources may be capable of being operated only during specified time sequences such as in coordination with other activities during the 3DP printing cycle and may be either pulsed or substantially continuous.

The ultraviolet light source(s) may be chosen to provide ultraviolet light that is suitable to kill or damage microorganisms of interest. Microorganisms that may be killed or damaged by such ultraviolet light include bacteria, viruses, yeast, spores, fungi and protozoa. Such microorganisms contain proteins and nucleic acid (DNA, RNA), which absorb ultraviolet light. Damage inflicted on such microorganisms by ultraviolet light can include any of: photolysis; loss of colony-forming ability (death); inability to support phage growth (enzyme inactivation); and destruction of nucleic acid (damage of genetic information). The source(s) of ultraviolet light may be suitable to provide ultraviolet light in any one or more of the wavelength ranges which are named and approximately defined as: near ultraviolet (400 to 500 nanometers), UV-A (315 to 400 nanometers), UV-B (289 to 315 nanometers), and UV-C (100 to 280 nanometers).

As already described, one possibility is that the source(s) of ultraviolet light may be suitable to provide ultraviolet light which is substantially continuous. Substantially continuous illumination may have a duration at least of the order of seconds. Substantially continuous illumination is known to be useful for a variety of purposes in killing microorganisms. Substantially continuous ultraviolet light may be provided by fluorescence, halogen, mercury vapor, microwave-generated continuous light sources or other appropriate sources. Alternatively, the source(s) of ultraviolet light may be pulsed sources such as pulsed xenon lamps. Pulsed sources of ultraviolet light are available, for example, from Xenon Corporation (Woburn, Mass.). Pulsed illumination is known to be useful for killing or damaging microorganisms and in particular is believed to have a greater penetrating distance into material than continuous illumination. Pulse duration may have a duration of the order of tens or hundreds of microseconds, i.e., less than a millisecond, but during that short time the instantaneous power may be relatively intense.

For either substantially continuous sources or pulsed sources, the illumination may be characterized by its value integrated over time to describe a delivered total energy. The source(s) may be suitable to provide, for example, illumination having an energy intensity of 1 to 3 Joules/cm^2 (integrated over a time period of interest) depending upon the type of microorganism which is desired to be killed or damaged. If the ultraviolet light is directed at powder, the apparatus may be suitable to deliver this integrated energy per unit surface area during each layer-forming cycle of the three-dimensional printing process. For some microorganisms, the energy intensity may be one or two orders of magnitude less than that intensity and still be sufficient. Required energy intensities as a function of microorganism that is desired to be killed or damaged, and as influenced by the wavelength of ultraviolet light, are known in the art (for example, at http://www.xenoncorp.com).

It is possible that what is described herein as a UV light source may also emit light in other regions of the electromagnetic spectrum, such as visible or even infrared, without departing from the present invention. Any UV light source described herein may be combined with optical filters which are suitable to modify what wavelengths from the source are transmitted to the machine or powder or other objects being illuminated. Intensities, wavelengths, pulse durations and other parameters may be chosen so as to kill or damage microorganisms of interest, as may be appropriate for a particular article and purpose. Any UV light source described herein may be surrounded in appropriate places by a shield to limit or direct where the emitted UV light goes. Such shields may shield certain components or regions of the machine from ultraviolet light, or may shield operating personnel from ultraviolet light.

Figure 3:
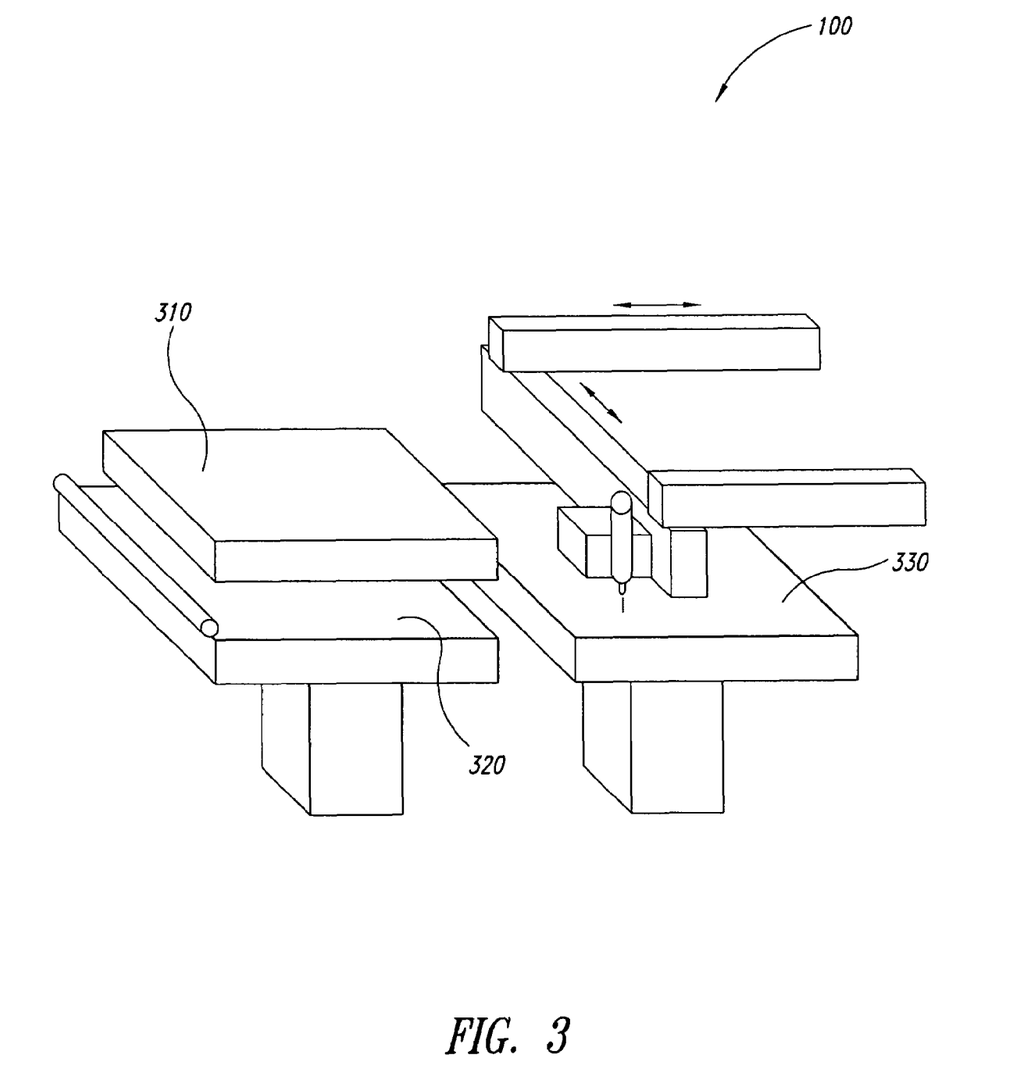
FIG. 3 illustrates a three-dimensional printing machine equipped with an illumination assembly that is movable and can be positioned in different locations within the machine at different times in accordance with principles of the present invention.

The ultraviolet light sources described so far have been stationary or fixed with respect to the overall machine. However, it is not necessary that they be stationary. Another possibility is that the 3DP machine may comprise at least one movable ultraviolet light source 310 that is movable with respect to the overall 3DP machine 100. This is illustrated in FIG. 3. The operating parameters of such a movable UV light source may be similar to those already described for a stationary UV light source. Movable UV light source 310 may, for example, be movable such that it can be positioned over and be capable of illuminating feed bed 320, and can be removed from the position over the feed bed.

It is, additionally or instead, possible that the movable UV light source may be movable such that it can be positioned over and be capable of illuminating build bed 330, and can be removed from the position over the build bed. The machine may comprise a motion control system capable of moving the movable ultraviolet light source into prescribed positions at prescribed times. Such motion control system may be the same as or different from the motion control system which moves the roller in the 3DP machine. Movable illumination sources or assemblies as described here allow the illumination to be positioned close to the powder when illumination is desired, improving the intensity of illumination, while also allowing other machine components to approach closely to the powder when the illumination assembly is removed from such position.

Co-pending commonly assigned patent application U.S. Ser. No. 10/189,795 has described an illumination assembly which comprised infrared light sources and which was movable. The 3DP machine of the present invention may comprise a movable UV light source that is similar to the illumination assembly described in that patent application. The 3DP machine may have an illumination assembly that comprises both UV light sources and infrared light sources in a single illumination assembly. The 3DP machine may have individually both a UV illumination assembly and an infrared illumination assembly, which assemblies may be moved by the same or different motion control systems.

Ultraviolet light sources as so far described have been suitable to illuminate the powder at times when the powder is stationary. It is also possible that the 3DP machine may comprise ultraviolet light sources that are conFIGured so as to direct ultraviolet light at the powder as the powder is being moved or spread, in addition to (or even instead of) directing ultraviolet light at the powder while the powder is stationary.

Spreading of powder, such as by a roller, is a dynamic process. During roller spreading, there is created ahead of the roller a ridge or pile of powder that may be termed a "dynamic pile" of powder that is advanced by the roller as the roller translates (and possibly also rotates). As the roller passes over the feed bed and collects powder from the feed bed, the dynamic pile grows. As the roller passes over the build bed and leaves powder deposited on the build bed, forming a newly deposited powder layer on the build bed, the dynamic pile shrinks. During these processes, powder particles are continually being mixed or stirred or agitated and change their positions with respect to each other and to the surface of the pile, and this may bring to an exposed surface of the dynamic pile some powder particles that may have been more interiorly as the powder lay stationary in the feed bed. It is possible to provide UV light sources that are suitable to illuminate powder during this dynamic situation suitably to provide disinfection or sterilization of the powder.

Figures 4A, 4B:
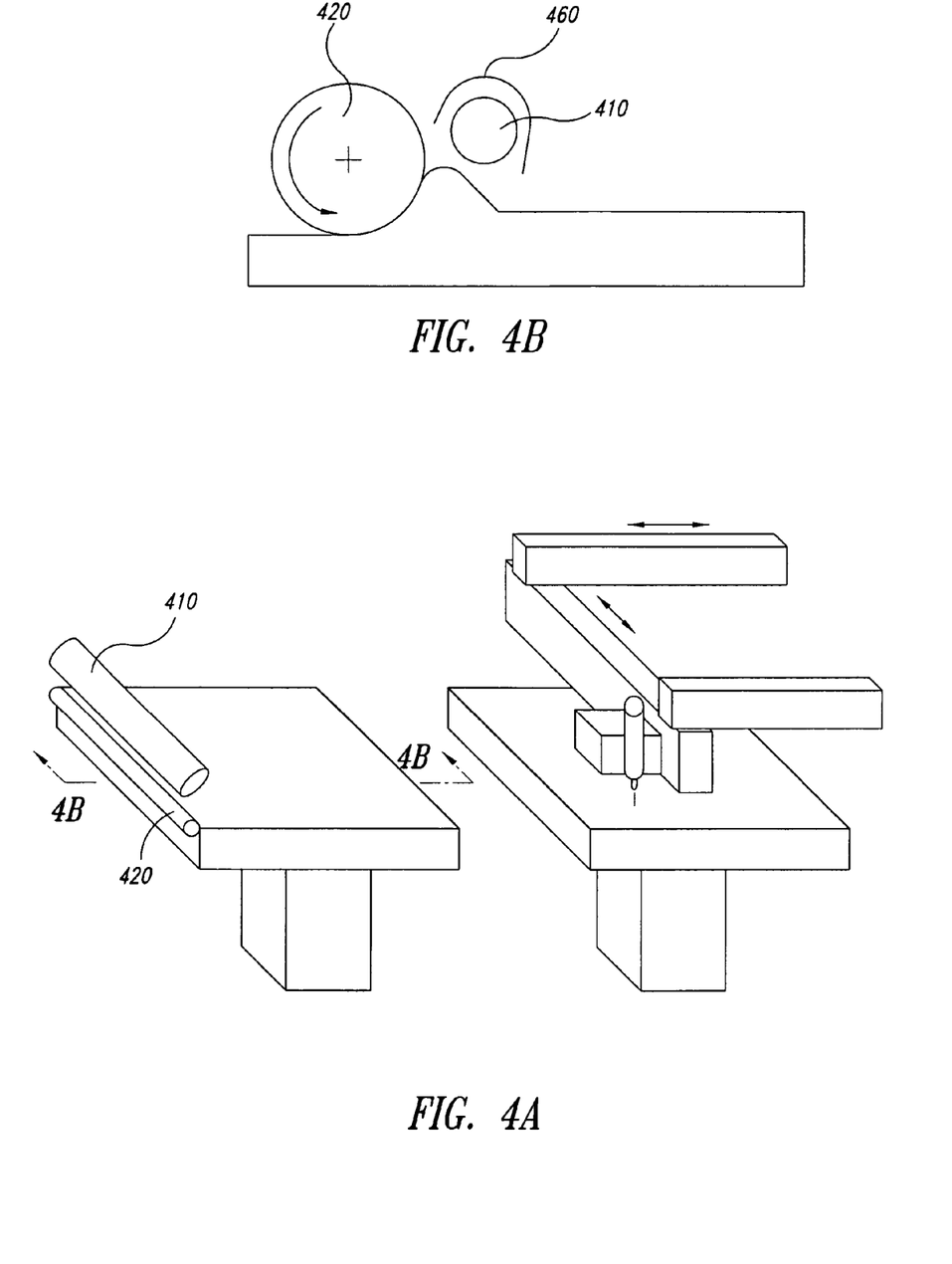
FIGS. 4A and 4B illustrate a three-dimensional printing machine equipped with a UV light source that is near the roller and travels with the roller so as to illuminate the dynamic pile of powder as the powder is being spread in accordance with principles of the present invention.

One such possibility is that there may be provided an ultraviolet light source 410, directed at the dynamic pile, which travels together with the roller 420 during spreading. This is illustrated in FIGS. 4A and 4B.

Figure 5A:
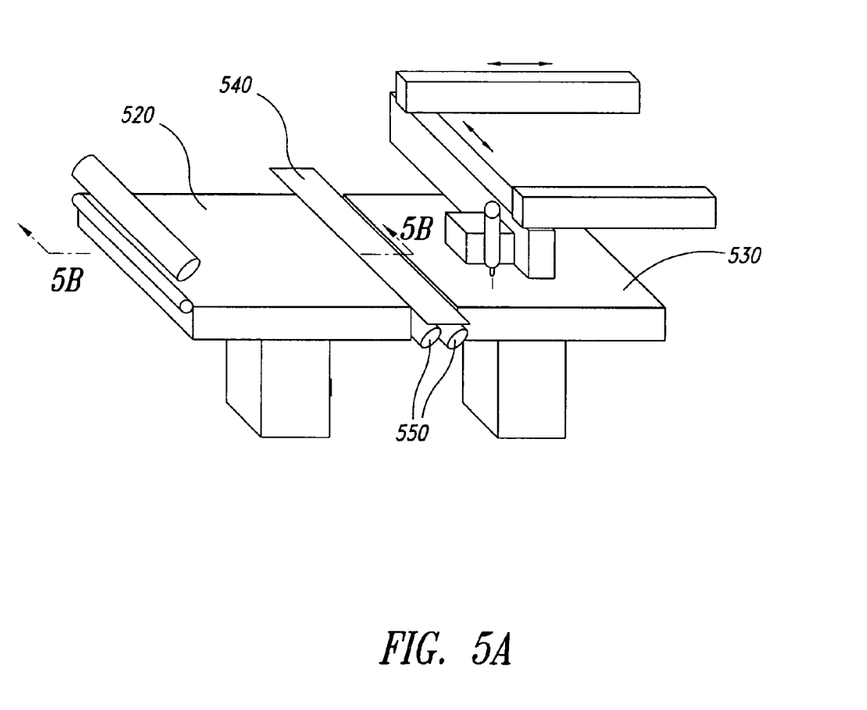
FIGS. 5A and 5B illustrate a UV light source located underneath a transparent platen over which powder slides while being spread, thereby providing UV illumination to the powder from underneath in accordance with principles of the present invention.
Figure 5B:
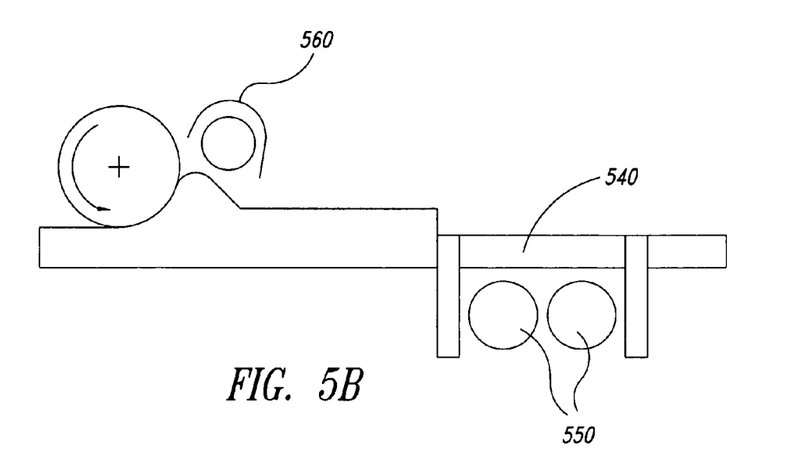

Another embodiment is illustrated in FIGS. 5A and 5B also in connection with the movement of the powder from the feed bed to the build bed. It is possible that the powder may be exposed to ultraviolet light from underneath, as it is moving. Between the feed bed 520 and the build bed 530, the 3DP machine may include a platen 540 over which powder slides on its way from the feed bed 520 to the build bed 530. That platen 520 may be at least partially transparent to ultraviolet light and there may be provided an ultraviolet light source 550 underneath platen 540, thereby exposing the underside of the powder pile to ultraviolet illumination as the powder pile passes over it.

Figure 6:
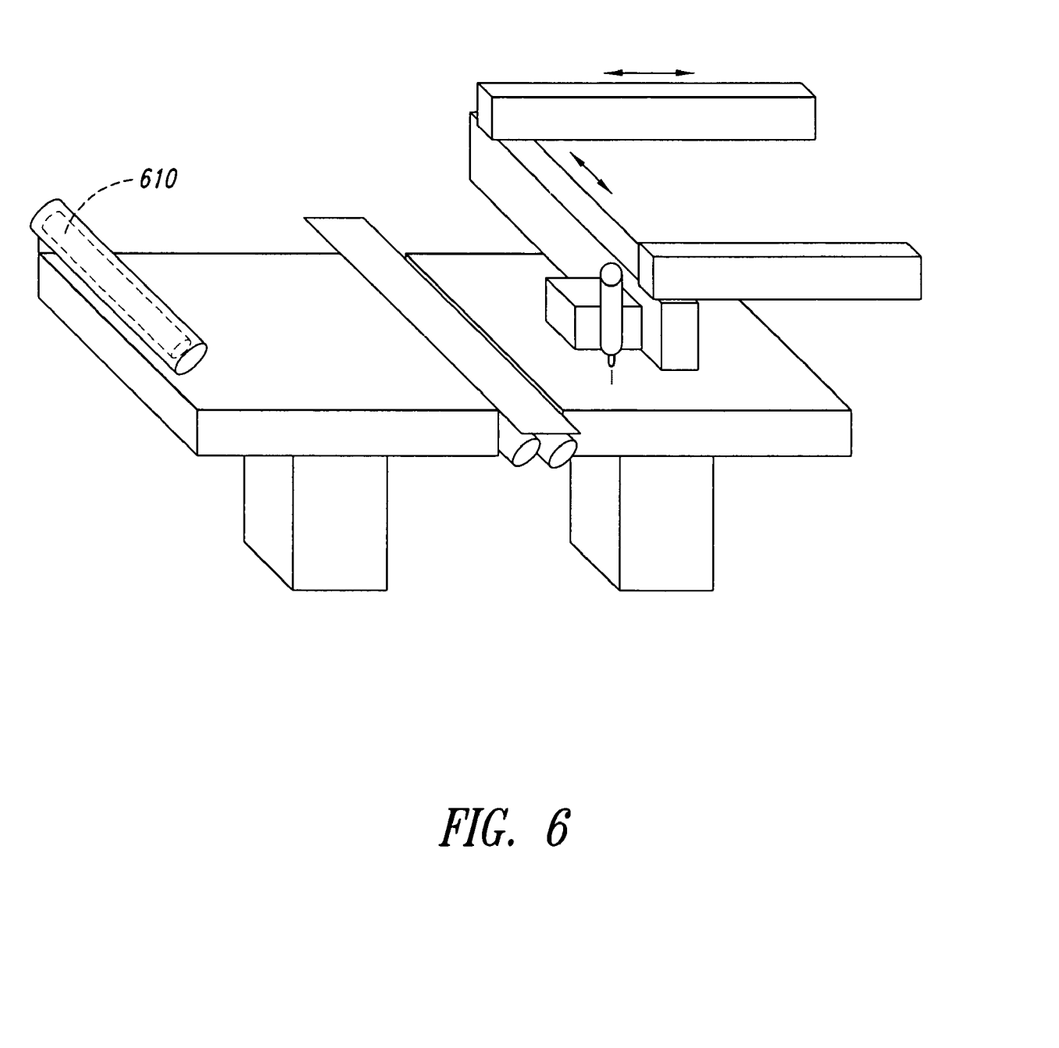
FIG. 6 illustrates an internally illuminated roller that exposes powder to ultraviolet light as the powder is being spread by the roller in accordance with principles of the present invention.

Yet another possibility is that the roller 610 may be at least partially transparent to ultraviolet light and may contain within itself a source of ultraviolet light. This embodiment is illustrated in FIG. 6.

In the manufacturing of medical articles, it is possible that liquid that is dispensed during the 3DP process may comprise substances that are fragile in the sense that they could be decomposed or damaged by exposure to ultraviolet light. If this is the case, with either stationary or movable UV sources, the sources may be positioned and/or their operation may be capable of being sequenced in time such that already-dispensed fragile substances are not exposed to excessive amounts of ultraviolet light and already-printed layers are not exposed to excessive amounts of ultraviolet light. Shields may be provided to direct UV light appropriately, shown in FIG. 4B as 460 and in FIG. 5B as 560. For example, the ultraviolet source may be directed only at locations outside of the build bed.

Alternatively, it is possible that the substances being dispensed from the printhead or dispenser may not vulnerable to damage by ultraviolet light. In this situation, those substances may be dispensed at any time relative to ultraviolet illumination. In this situation, the apparatus may be arranged and sequenced such that already-dispensed binder liquid is included among the things that are exposed to ultraviolet light. It is also possible that the apparatus may direct ultraviolet light at liquid in a partially transparent or transparent tube or a tube having windows to allow the ultraviolet light to sterilize or disinfect the liquid as the liquid is brought to the printhead or dispenser. The liquid may be brought to the printhead or dispenser by supply conduits which may be chosen to be at least partially transparent to ultraviolet light and which may be illuminated by ultraviolet light so as to kill or damage microorganisms which may be present in the liquid or fluid in those conduits.

The invention may comprise any combination of any number of the disclosed arrangements for exposing things to ultraviolet light.

The present invention may include apparatus suitable to provide ultraviolet light having characteristics suitable to polymerize or cross-link substances of interest such as binder substances. Such polymerization or cross-linking may be simultaneous with or separate from the exposure for purposes of sterilization or disinfection. If ultraviolet light is provided for the purpose of cross-linking or polymerization, that light may be the same as or different from the ultraviolet light which is provided for purposes of sterilization or disinfection. For example, ultraviolet light for cross-linking or polymerization may be either substantially continuous or pulsed, and ultraviolet light for sterilization or disinfection may be either substantially continuous or pulsed, in any combination. The Wavelengths of ultraviolet light for these two purposes could be different, if desired, as appropriate for each individual purpose. The apparatus which provides ultraviolet light for one purpose may be the same as or distinct from the apparatus which provides ultraviolet light for the other purpose.

The ultraviolet light apparatus as described herein may be included on the three-dimensional printing machine in conjunction with other apparatus directed toward cleanliness and/or disinfection and/or sterility of the three-dimensional printing machine. For example, appropriate enclosure and ventilation of the 3DP machine or regions thereof may be provided, including particulate removal filters and other similar means, as described in the referenced commonly assigned co-pending patent application, which is incorporated herein by reference. Apparatus may be provided for circulating in the vicinity of the machine, at designated times, a disinfectant and/or steriliant gas or vapor such as ethylene oxide, hydrogen peroxide vapor, or other substances as are known in the relevant art.

Method of Three-Dimensional Printing Including Ultraviolet Light

The present invention also comprises methods of performing three-dimensional printing while using illumination by ultraviolet light. The method may comprise presenting powder in a feed bed, spreading powder from the feed bed to a build bed such as by a roller, and printing upon the powder in the build bed by dispensing onto it in appropriate places a binder liquid. Other methods of depositing powder, such as slurry deposition, could also be used. While the powder is at the top of the feed bed, or while the powder is being moved from the feed bed to the build bed, or even after the powder is in place on the build bed, the powder may be illuminated by ultraviolet light under appropriate conditions to kill or damage microorganisms. Whether the build bed illumination (if used) is performed before or after dispensing may depend on whether the binder is or is not undesirably affected by ultraviolet light. The method may comprise directing stationary ultraviolet light sources at appropriate places and/or may comprise moving an illumination assembly into and out of position over the feed bed or build bed or both, may comprise directing ultraviolet light at powder which is stationary and/or directing ultraviolet light at powder which is in motion while being spread.

More generally, the present invention comprises the practice of disinfecting or sterilizing an article layer-by-layer as the article is being built up in a layer-by-layer manner. Also, the present invention comprises exposing powder to ultraviolet light during any manufacturing operation in which powder is assembled to form an article.

The method may include exposing binder liquid to ultraviolet light as the binder liquid travels to the printhead.

The method may include exposing the powder or machine parts to either pulsed or continuous ultraviolet light or both, as appropriate, of whatever wavelength is appropriate, during or between whatever stages of three-dimensional printing might be appropriate. If ultraviolet light is directed at powder, the mentioned integrated energy per unit area, such as approximately 1 Joule/cm^2, may be directed at powder during each layer-by layer repetition of the steps of the three-dimensional printing process. The method may include using ultraviolet light to cause curing or cross-linking of a binder substance used in the three-dimensional printing process, in addition to using the ultraviolet light to sterilize or disinfect.

The method may include exposing the machine or parts of it to a steriliant gas or vapor such as ethylene oxide, hydrogen peroxide vapor, or other substances as are known in the relevant art.

The method may include exposing powder to ultraviolet light at appropriate times and in appropriate ways such that the dispensed substance(s) that is delivered through the printhead is never exposed to ultraviolet light to any substantial degree; rather, only powder may be so exposed. This may be appropriate if at least some component of the dispensed substance might be damaged by exposure to ultraviolet light. Alternatively, it is possible that the dispensed substance(s) might not be undesirably damaged by exposure to ultraviolet light. In this case, it is possible that both the powder and the dispensed substance may be exposed to ultraviolet light at some point during the processing of each layer of the three-dimensional printing process or other layered manufacturing process.

The method may also include exposing to ultraviolet light portions of the three-dimensional printing machine itself, such as surfaces that may come into contact with powder during normal operation of the machine.

Techniques for cleanliness control, disinfection, sterility etc. may be employed in any liquid or fluid handling systems and/or powder handling systems involved in the 3DP machine. Any combination of such techniques may be employed.

The invention also includes an article made by any of the described methods.

Further Comments

The use of ultraviolet light as described can first of all kill or damage microorganisms, which is itself desirable. In addition, killing or damaging microorganisms at a relatively early stage of manufacturing of an article, may prevent the microorganisms from reproducing and multiplying during subsequent stages of manufacturing prior to terminal sterilization (if terminal sterilization is used). Bioburden is a term referring the quantity of dead microorganisms present in an article. For some medical articles even dead microorganisms are objectionable and so bioburden may have to be minimized. The use of ultraviolet light during powder handling and on the machine as described herein helps to achieve that goal.

This invention is also advantageous in that it is less damaging to fragile biological substances than other forms of sterilization/disinfection. Thus, fragile biological substances can be exposed to something less damaging than other forms of sterilization. Another advantage of the present invention is that the powder can be separately sterilized from the binder, thus allowing the binder to carry biological carriers that cannot tolerate sterilization. The layered nature of the manufacturing and the handling of powder means that at least the powder component of the article can be sterilized/disinfected close to the time that it is incorporated into the actual article, without exposing the biological substances to ultraviolet light.

Commonly assigned co-pending U.S. patent application U.S. Ser. No. 10/189,795 describes illumination assemblies, and U.S. Ser. No. 10/189,166 describes ventilation and enclosure and aseptic aspects. All patents and applications cited above are incorporated by reference in their entirety. The above description of illustrated embodiments of the invention is not intended to be exhaustive or to limit the invention to the precise form disclosed. While specific embodiments of, and examples for, the invention are described herein for illustrative purposes, various equivalent modifications are possible within the scope of the invention, as those skilled in the relevant art will recognize. Aspects of the invention can be modified, if necessary, to employ the process, apparatuses and concepts of the various patents and applications described above to provide yet further embodiments of the invention. These and other changes can be made to the invention in light of the above detailed description. In general, in the following claims, the terms used should not be construed to limit the invention to the specific embodiments disclosed in the specification and the claims, but should be construed to include all methods, apparatus and articles that operate under the claims. Accordingly, the invention is not limited by the disclosure, but instead the scope of the invention is to be determined entirely by the following claims.

From the foregoing it will be appreciated that, although specific embodiments of the invention have been described herein for purposes of illustration, various modifications may be made without deviating from the spirit and scope of the invention. Accordingly, the invention is not limited except as by the appended claims.

We claim:

1. A three-dimensional printing machine comprising at least one ultraviolet light source suitable to kill or damage microorganisms, wherein at least one ultraviolet source is substantially stationary.

2. The apparatus of claim 1, wherein at least one ultraviolet source is a source suitable to operate substantially continuously for a time period of at least 1 second.

3. The apparatus of claim 2, wherein the continuous ultraviolet source is suitable to operate during substantially all portions of a three-dimensional printing process.

4. The apparatus of claim 2, wherein the continuous ultraviolet source is suitable to operate during only certain portions of a three-dimensional printing process.

5. The apparatus of claim 1, wherein at least one ultraviolet source is a pulsed source suitable to operate for periods of less than a millisecond at any individual pulse.

6. The apparatus of claim 5, wherein the pulsed ultraviolet source is suitable to operate during substantially all portions of a three-dimensional printing process.

7. The apparatus of claim 5, wherein the pulsed ultraviolet source is suitable to operate during only certain portions of a three-dimensional printing process.

8. The apparatus of claim 1, wherein at least one ultraviolet source is suitable to be directed at powder that is stationary.

9. The apparatus of claim 1, wherein at least one ultraviolet light source is directed or is capable of being directed at components of the machine that contact powder at least some time during normal operation of the machine.

10. The apparatus of claim 1, wherein at least one ultraviolet source is capable of providing a total energy, integrated over a period of time of interest, of at least approximately 1 Joule/cm^2.

11. The apparatus of claim 10, wherein the period of time of interest is one cycle of a three-dimensional printing process.

12. The apparatus of claim 1, wherein at least one ultraviolet source is capable of killing or damaging microorganisms in a powder bed to a depth of at least approximately 300 micrometers.

13. The apparatus of claim 1, wherein the three-dimensional printing machine defines a thickness of layer used in performing three-dimensional printing, and at least one ultraviolet source is capable of killing or damaging microorganisms in a powder bed to a depth at least as large as the layer thickness.

14. The apparatus of claim 1, wherein at least one ultraviolet source is also suitable to polymerize or cross-link a substance.

15. The apparatus of claim 14, wherein the polymerization or cross-linking ultraviolet source is the same as the sterilization or disinfection ultraviolet source.

16. A three-dimensional printing machine comprising at least one ultraviolet light source suitable to kill or damage microorganisms, wherein at least one ultraviolet source is suitable to be moved into a position substantially over a feed bed, illuminated, and then moved out of the position that was substantially over the feed bed.

17. The apparatus of claim 16, wherein at least one ultraviolet source is suitable to be moved into a position substantially over a build bed, illuminated, and then moved out of the position that was substantially over the build bed.

18. The apparatus of claim 16, wherein at least one ultraviolet source is suitable to be moved while it is illuminated.

19. A three-dimensional printing machine comprising at least one ultraviolet light source suitable to kill or damage microorganisms, wherein at least one ultraviolet source is suitable to be moved while it is illuminated, wherein at least one ultraviolet source is suitable to translate as a powder-spreading roller translates.

20. A three-dimensional printing machine comprising at least one ultraviolet light source suitable to kill or damage microorganisms, wherein at least one ultraviolet source is suitable to be directed at powder that is moving.

21. A three-dimensional printing machine comprising at least one ultraviolet light source suitable to kill or damage microorganisms, wherein at least one ultraviolet source is located underneath a transparent platen over which powder travels as it moves between a feed bed and a build bed.

22. A three-dimensional printing machine comprising at least one ultraviolet light source suitable to kill or damage microorganisms, wherein at least one ultraviolet source is located inside an at least partially transparent roller which is suitable to move powder from a feed bed to a build bed.

23. A three-dimensional printing machine comprising at least one ultraviolet light source suitable to kill or damage microorganisms, wherein at least one ultraviolet light source is directed or is capable of being directed at a powder feed bed.

24. A three-dimensional printing machine comprising at least one ultraviolet light source suitable to kill or damage microorganisms, wherein at least one ultraviolet source is also suitable to polymerize or cross-link a substance, wherein the polymerization or cross-linking ultraviolet source is different from the sterilization or disinfection ultraviolet source.

25. A three-dimensional printing machine comprising at least one ultraviolet light source suitable to kill or damage microorganisms, further comprising an optical filter disposed to filter light from at least one ultraviolet source.

26. A three-dimensional printing machine comprising at least one ultraviolet light source suitable to kill or damage microorganisms, further comprising a shield in proximity to at least one ultraviolet source.

27. A three-dimensional printing machine comprising at least one ultraviolet light source suitable to kill or damage microorganisms, wherein at least one ultraviolet source is directed at an at least partially transparent conduit that carries liquid to a dispenser in the three-dimensional printing machine.

28. A three-dimensional printing machine comprising at least one ultraviolet light source that is or is capable of being directed at a powder feed bed.

29. The apparatus of claim 28, wherein said at least one ultraviolet source is a source suitable to operate substantially continuously for a time period of at least 1 second.

30. The apparatus of claim 29, wherein said at least one ultraviolet source suitable to operate substantially continuously is suitable to operate during substantially all portions of a three-dimensional printing process.

31. The apparatus of claim 29, wherein said at least one ultraviolet source suitable to operate substantially continuously is suitable to operate during only certain portions of a three-dimensional printing process.

32. The apparatus of claim 28, wherein said at least one ultraviolet source is a pulsed source suitable to operate for periods of less than a millisecond at any individual pulse.

33. The apparatus of claim 32, wherein the pulsed ultraviolet source is suitable to operate during substantially all portions of a three-dimensional printing process.

34. The apparatus of claim 32, wherein the pulsed ultraviolet source is suitable to operate during only certain portions of a three-dimensional printing process.

35. The apparatus of claim 28, wherein at least one ultraviolet source is suitable to be moved into a position substantially over a build bed, illuminated, and then moved out of the position that was substantially over the build bed.

36. The apparatus of claim 28, wherein at least one ultraviolet source is suitable to be moved while it is illuminated.

37. The apparatus of claim 28, wherein at least one ultraviolet source is suitable to be directed at powder that is stationary.

38. The apparatus of claim 28, wherein at least one ultraviolet light source is directed or is capable of being directed at components of the machine that contact powder at least some time during normal operation of the machine.

39. The apparatus of claim 28, wherein at least one ultraviolet source is capable of provided a total energy, integrated over a period of time of interest, of at least approximately 1 Joule/cm^2.

40. The apparatus of claim 39, wherein the period of time of interest is one cycle of a three-dimensional printing process.

41. The apparatus of claim 28, wherein at least one ultraviolet source is capable of killing or damaging microorganisms in a powder bed to a depth of at least approximately 300 micrometers.

42. The apparatus of claim 28, wherein the three-dimensional printing machine defines a thickness of layer used in performing three-dimensional printing, and at least one ultraviolet source is capable of killing or damaging microorganisms in a powder bed to a depth at least as large as the layer thickness.

43. The apparatus of claim 28, wherein at least one ultraviolet source is also suitable to polymerize or cross-link a substance.

44. The apparatus of claim 43, wherein the polymerization or cross-linking ultraviolet source is the same as the sterilization or disinfection ultraviolet source.

45. The apparatus of claim 28, wherein said at least one ultraviolet light source is suitable to kill or damage microorganisms.

* * * * *